United States Patent [19]

Hill

[11] Patent Number: 4,852,412

[45] Date of Patent: Aug. 1, 1989

[54] SAMPLING THE CONTENTS OF PRESSURISED VESSELS

[75] Inventor: Derek A. Hill, Basingstoke, England

[73] Assignee: Baker Perkins PLC, Great Britain

[21] Appl. No.: 102,873

[22] Filed: Sep. 30, 1987

[30] Foreign Application Priority Data

Oct. 3, 1986 [GB] United Kingdom ............... 8623834

[51] Int. Cl.⁴ .................. G01N 1/00; G01N 35/00
[52] U.S. Cl. .................. 73/863.85; 73/863.86
[58] Field of Search ........... 73/864.63, 863.85, 863.86, 73/861.18

[56] References Cited

U.S. PATENT DOCUMENTS

| | | | |
|---|---|---|---|
| 2,752,228 | 6/1956 | Gould | 73/864.64 |
| 4,294,124 | 10/1981 | Kalwaitis | 73/863.85 |
| 4,375,170 | 3/1983 | Sperry, III et al. | 73/863.85 |
| 4,471,664 | 9/1984 | Mailliet et al. | 73/863.85 |
| 4,631,961 | 12/1986 | Yohe et al. | 73/863.85 |
| 4,669,321 | 6/1987 | Meyer | 73/863.85 |
| 4,682,508 | 7/1987 | Steiner et al. | 73/863.85 |
| 4,742,717 | 5/1988 | Ichino | 73/861.18 |

*Primary Examiner*—Stewart J. Levy
*Assistant Examiner*—Robert P. Bell
*Attorney, Agent, or Firm*—Steele, Gould & Fried

[57] ABSTRACT

Apparatus 1 for sampling the contents of a pressurised vessel 2 comprises a valve 3 having an inlet 4 and an outlet 5. The inlet 4 is in communication with the interior of the vessel 2. A sample-receiving pressure receptacle 7 is connectable to the valve outlet 5 in a sealing manner, and a pressure venting line 8 is provided for equalizing the interior of the receptacle 7 with the atmosphere. When the valve 3 is open, a sample of pressurized vessel contents can enter the receptacle 7. When the valve is then closed, the sample remains in the receptacle 7. A probe 31, operable from outside the pressurized vessel 2, is provided so that, when the valve 3 is open, a sample of the vessel contents can be drawn through the valve and into the receptacle 7.

8 Claims, 1 Drawing Sheet

SAMPLING THE CONTENTS OF PRESSURISED VESSELS

BACKGROUND OF THE INVENTION

This invention relates to apparatus for sampling the contents of pressurized vessels.

As used herein, the term "pressurized vessels" is intended to cover pressure vessels operable with internal pressures both above and below atmospheric.

While the invention can be applied to pressurized vessels carrying out a number of differing processes, it has particular application to pressurized vessels for cooking food products.

It is a requirement that samples of a product being processed in a pressurized vessel be obtained at points during the process cycle, so as to monitor the processing in order to terminate it at the optimum time.

Known sampling systems require equalizing the interior of a pressurised vessel to that of the ambient atmosphere, opening up the vessel, removing a sample, resealing the vessel, and then restoring its internal pressure.

Disadvantages of such systems are:
1. The time necessary to bring the internal pressure of the vessel to atmospheric, and then to restore the vessel to the process conditions, is not consistent with normal production cycles;
2. The sample cannot be truly representative because of the lengthy procedure, and
3. The process would continue to a varying extent while equalization with atmospheric pressure is being achieved, such that it is difficult to pinpoint the actual stage in the process cycle reached when the sample was taken.

With the present invention there is no need to equalize the internal pressure of the vessel with the atmosphere in order to allow a sample to be taken. The sample can therefore be taken without interrupting the process cycle. Furthermore, the time at which the sample is taken can be accurately related to a particular point in the uninterrupted process cycle, and therefore relate more precisely to the state or stage of development reached by the product being processed such that the optimum moment for terminating the processing cycle can be determined.

SUMMARY OF THE INVENTION

According to the invention, apparatus for sampling the contents of a pressurised vessel comprises a valve having an inlet and an outlet, the inlet intended to be in communication with the interior of the vessel, a sample-receiving pressure receptacle connectable to the valve outlet in a sealing manner, and means for equalizing the interior of the receptacle with the atmosphere.

When the valve is opened, a sample of contents of the pressurised vessel can enter the pressure receptacle and when the valve is then closed, the sample remains in the receptacle.

The apparatus may be provided with sample withdrawal means, operable from outside the pressurised vessel, whereby, when the valve of the pressurised vessel is opened, a sample of the vessel contents can be displaced through the valve and into the receptacle.

The invention also comprises the combination of a pressurised vessel and the novel apparatus for sampling its contents.

The invention also comprises any novel subject matter or combination including novel subject matter herein disclosed.

BRIEF DESCRIPTION OF THE DRAWINGS

An embodiment of the invention will now be described by way of example only, with reference to the accompanying drawings, wherein.

DETAILED DESCRIPTION OF THE PREFERRED EMBODIMENT

Figure 2:
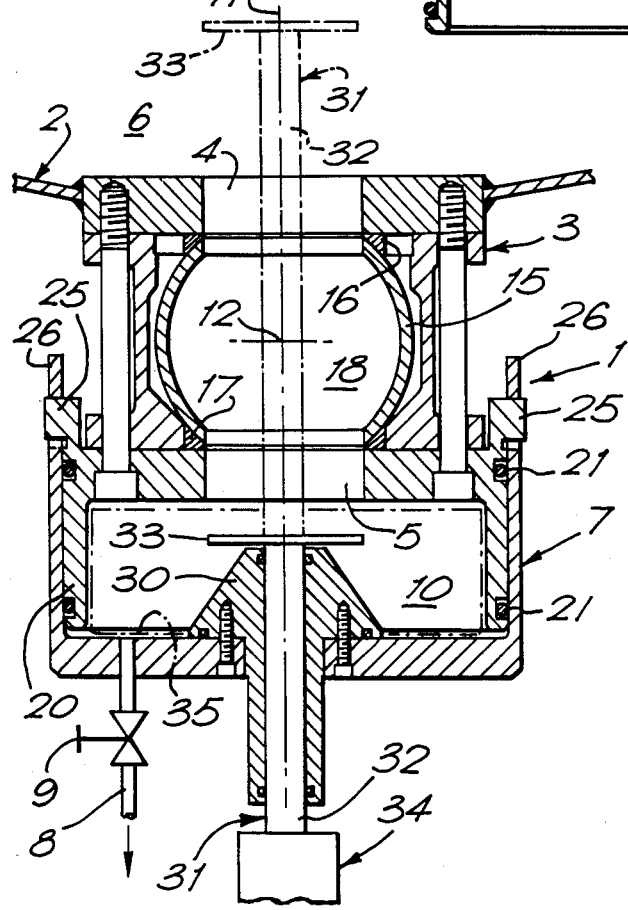
FIG. 2 is a side view, again in medial section, of the complete apparatus.

With reference first to FIG. 2, apparatus 1 for sampling the contents of a pressurised cooking vessel 2 without need to equalize the pressure therein with the atmospheric pressure is illustrated thereby. The apparatus 1 comprises a valve 3 connected thereto, the valve having an inlet 4 and an outlet 5 aligned with each other on a common central axis 11. The valve inlet 4 is in communication with the interior 6 of the vessel 2. The apparatus 1 further comprises a sample-receiving pressure receptacle 7 demountably connected to the valve outlet 5 in a sealing manner. Means comprising a pressure venting line 8 with a bleed valve 9 are provided for equalising the interior 10 of the receptacle 7 with the ambient atmosphere.

Figure 1:
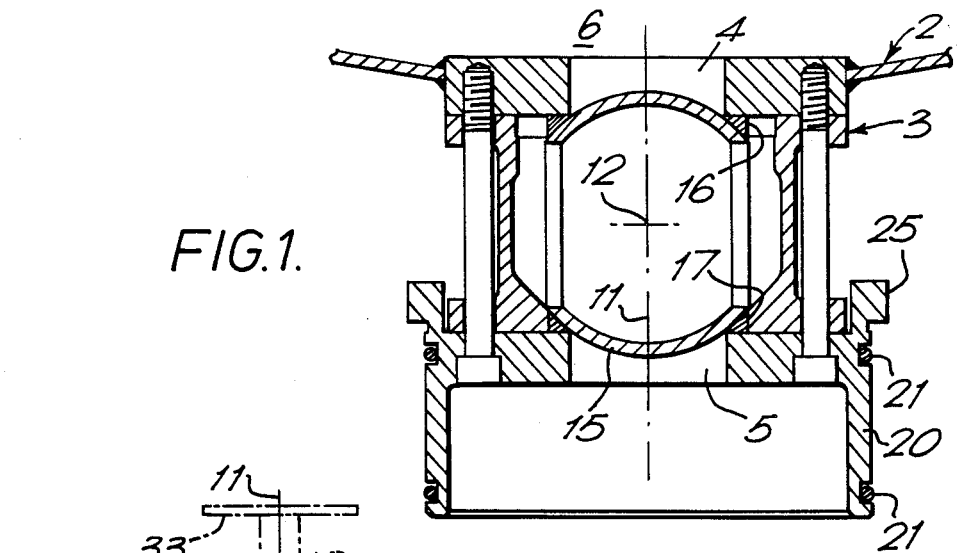
FIG. 1 is a side view, in medial section, of part of a pressurised vessel with the valve of the invention connected thereto.

The pressurised vessel 2 of this example is used for cooking cereal. The valve 3 is a stainless "ball" valve, comprising a generally spherical valve member 15 cooperable with upper and lower oppositely-disposed part-spherical seats 16, 17. The valve 3 illustrated is known as a "Worcester Ball Valve". The ball valve member 15 is rotatable about an axis 12 disposed substantially normal to the valve seat axis 11, and is operable between closed (FIG. 1) and open (FIG. 2) positions by conventional valve operating means, not shown. The valve member 15, which is hollow, has oppositely-disposed openings which, with its interior define a central flow passageway 18 extending through the valve member.

The valve 3 has a lower portion in the form of a downwardlyextending bell flange 20 with axially-spaced sealing rings 21 disposed in the outer face thereof. The receptacle 7 has an upper, bell or cup-shaped portion which fits over the bell flange 20 as shown in FIG. 2, the rings 21 providing a good seal between the two interfitting bell-shaped components.

The pressure receptacle 7 is demountably secured in place by bayonet coupling means comprising lugs 25 forming part of the valve 3, which cooperate with hooks 26 forming part of the receptacle. The pressure receptacle 7 is actually secured in place by a slight turning motion applied thereto, until the lugs 25 and hooks 26 interfit.

The pressure receptacle 7 has a central gland or stuffing box 30 through which a probe 31 carried by the receptacle passes lengthwise in a sealed manner, along the axis 11. The probe 31 comprises a rod 32 which carries on its upper end a disc-like plate 33. The lower end of the rod 32 is attached to a double action piston and cylinder type fluid actuator 34 by means of which the probe 31 is made movable relative to the receptacle 7. Thus the plate 33 can be raised (when the valve 3 is open) from a retracted position (full lines) to a raised position (chain-dotted lines) within the vessel 2, extending through the passageway 18 of the valve member 15 as it does so, and then returned to the retracted position.

In operation, to remove a sample from the interior of the vessel 2 when pressurised, the pressure receptacle 7 is fitted to the bell flange 20, with the probe 31 in the retracted position, and the bleed valve 9 closed.

With the pressure receptacle 7 firmly secured in place, by means of the coupling together of the lugs 25 and hooks 26, confirmed by valve interlock controls (not shown), the valve 3 is opened, so that the internal pressure of the receptacle 7 equalizes to that of the vessel 2, whereupon the probe 31 is moved to its raised position, (chain-dotted lines), so as to engage with material being cooked. Upon retraction of the probe 31, a sample of the material engaged by the plate 33 is drawn through the valve passageway 18 and into the receptacle 7. This drawing or "raking" action of the probe 31 and plate 33 carried thereby can be repeated until sufficient material for the sampling purposes has been transferred to the pressure receptacle 7. With the probe 31 in the retracted position (full lines), the valve 3 can be closed. Next, the bleed valve 9 is opened in order to vent the receptacle 7 to atmosphere. When the safety interlock controls indicate that the internal pressure of the receptacle 7 is such that the receptacle 7 can be safely uncoupled, the receptacle is removed and the sample collected therein taken away for analysis.

The pressure receptacle 7 may have a liner 35 which can be removed to make it easier to lift sample material out of the receptacle.

The probe 31 is only used if the contents of the pressurised vessel 2 are not of a free-flowing nature. If the product is free-flowing, the sample can be taken simply by slightly opening the valve 3 and allowing sufficient material to enter the receptacle 7.

Employing as it does a well-tried and accepted ball valve design, apparatus according to the invention meets all the standards required with pressurised vessels, It also makes the removal of samples a quicker operation, leading to much more precise analysis results, thus enabling more accurate termination of the treatment process.

In a non-illustrated modification, a probe 31, (or like device), is disposed within the pressurised vessel and is operable to extend downwardly through the passageway 18 and into the receptacle 7 by way of the valve inlet 4. Such a probe results in the application of a pushing action on material to be sampled.

If desired, the lugs 25 and hooks 26 form of coupling may be replaced by another form of demountable coupling.

I claim:

1. Apparatus for sampling the contents of a pressure vessel, comprising:
    a valve having an inlet connectable with the interior of the pressure vessel, and an outlet;
    a valve member disposed between the valve inlet and the valve outlet and defining a flow passageway therethrough;
    a sample-receiving receptacle sealably connectable to the valve outlet, the receptacle having an interior which is connectable with said passageway by means of said valve member, and which is substantially larger in cross-section than said passageway;
    a probe carried by the receptacle and movable relative to the receptacle, the probe having an enlarged rake head, said head formed such that a sample of the vessel's contents can be raked through the valve passageway and into the receptacle; and,
    means for atmospherically equalizing the pressure in the interior of receptacle.

2. Apparatus as claimed in claim 1, further comprising means operable from outside said vessel for moving the probe when the pressure vessel is opened.

3. Apparatus as claimed in claim 1, wherein the valve member is generally spherical and cooperates with oppositely-disposed and aligned part-spherical valve seats, the valve member having a flow passageway extending therethrough.

4. Apparatus as claimed in claim 1, wherein the valve has a lower, bell-shaped portion, and the receptacle has a cooperating upper, bell-shaped portion, the two bell-shaped portions interfitting one with the other.

5. Apparatus as claimed in claim 4, further comprising means for releasably coupling the receptacle to the valve outlet.

6. Apparatus as claimed in claim 1, wherein the means for atmospherically equalizing the pressure in the interior of the receptacle comprises a pressure venting line and a bleed valve connected to the venting line.

7. The combination of a pressurized vessel and apparatus as claimed in claim 1 sealably connected to the pressurized vessel.

8. Apparatus as claimed in claim 5, wherein the means for releasably coupling the receptacle to the valve outlet comprises a bayonet coupling.

* * * * *